(12) United States Patent
Palti

(10) Patent No.: US 8,715,191 B2
(45) Date of Patent: May 6, 2014

(54) DOPPLER BASED FLOW MEASUREMENTS

(75) Inventor: Yoram Palti, Haifa (IL)

(73) Assignee: Echosense Inc., Tortola (VG)

(*) Notice: Subject to any disclaimer, the term of this patent is extended or adjusted under 35 U.S.C. 154(b) by 501 days.

(21) Appl. No.: 12/771,091

(22) Filed: Apr. 30, 2010

(65) Prior Publication Data

US 2010/0280385 A1 Nov. 4, 2010

Related U.S. Application Data

(60) Provisional application No. 61/174,753, filed on May 1, 2009.

(51) Int. Cl.
*A61B 8/00* (2006.01)
*A61B 8/06* (2006.01)
*G01S 15/89* (2006.01)
*G01S 7/52* (2006.01)

(52) U.S. Cl.
CPC ............ *A61B 8/06* (2013.01); *G01S 15/8979* (2013.01); *G01S 7/52071* (2013.01)
USPC .......................................... 600/454; 600/455

(58) Field of Classification Search
CPC ........................................................ A61B 8/06
USPC ........................................................ 600/454
See application file for complete search history.

(56) References Cited

U.S. PATENT DOCUMENTS

| | | | |
|---|---|---|---|
| 4,848,354 A | 7/1989 | Angelsen et al. | |
| 5,471,990 A | 12/1995 | Thirsk | |
| 5,871,447 A | 2/1999 | Ramamurthy et al. | |
| 5,935,074 A * | 8/1999 | Mo et al. | 600/454 |
| 2005/0222506 A1* | 10/2005 | Takimoto et al. | 600/455 |
| 2007/0110191 A1* | 5/2007 | Kim et al. | 375/340 |
| 2008/0015763 A1* | 1/2008 | Kitazaki et al. | 701/70 |

FOREIGN PATENT DOCUMENTS

| | | | | |
|---|---|---|---|---|
| WO | 2007023438 | | 3/2007 | |
| WO | 2007073173 | | 6/2007 | |
| WO | WO 2007/073173 | * | 6/2007 | ............... G01S 7/41 |

OTHER PUBLICATIONS

"Buck et al.," "Flow Quantification in Valvular Heart Disease Based on the Integral of Backscattered Acoustic Power Using Doppler Ultrasound," Proceedings of the IEEE, vol. 88 No. 3, Mar. 2000.*
Search Report and Written Opinion from corresponding application PCT/IB2010/000987.

* cited by examiner

*Primary Examiner* — Tse Chen
*Assistant Examiner* — Patricia Park
(74) *Attorney, Agent, or Firm* — Proskauer

(57) ABSTRACT

A new approach to processing and displaying received Doppler signals is disclosed. This approach starts with a set of N power spectra corresponding to each of N times. Those power spectra are then used to create of set of pixels for display with respect to an X axis and a Y axis so that the X coordinate of each pixel in the set corresponds to a time and the Y coordinate of each pixel in the set corresponds to a quantized power level. An attribute (e.g., color or intensity) of each pixel in the set is set to represent the highest velocity for the time-and-quantized-power-level combination that corresponds to the X and Y coordinates of each pixel in the set.

13 Claims, 7 Drawing Sheets

DOPPLER BASED FLOW MEASUREMENTS

CROSS REFERENCE TO RELATED APPLICATIONS

This application claims priority to U.S. provisional application No. 61/174,753, filed May 1, 2009.

BACKGROUND

Measurement and monitoring of blood flow velocity is commonly carried out using ultrasound Doppler technology. Such flow measurements are primarily directed to peripheral arteries such as the carotid and femoral arteries as well as intra skull arteries by Trans-Cranial Doppler (TCD). Some devices capable in principle of measuring blood flow in the coronary arteries are available on the market. Many such cardiac devices are based on ultrasound cardiac imaging with the addition of Doppler velocity flow measurement capability which can be used for the coronary artery flow measurements. However the use of these devices is limited, due in part to the complexity and low sensitivity of the available technologies and measuring routines.

Two conventional modes are popular. The first mode is color Doppler imaging which, when directed appropriately, can display a very low resolution image of the flow direction with velocity indicated on a low resolution color scale. This mode is primarily designed to monitor flow directions rather than an accurate flow velocity monitoring vs. time.

In the second mode, the cardiac echo system is operated in imaging mode and the desired coronary artery is manually searched for. Echo operators that are highly trained for this task can identify a coronary artery, usually in cross section, and then direct to it a pointer that selects the identified area for using Doppler mode. In this case the coronary blood flow velocity at the selected point is displayed in real time. In these systems, a real time graphical display is generated in which the Y axis represents velocity and the X axis represents the running time. A low resolution indication of the power of the reflected ultrasound energy is provided using a gray scale (by assigning different intensities to different powers) or a color scale (by assigning different colors to different powers). The velocity of all elements, which move relative to the ultrasound beam, (for example, erythrocytes that flow at different velocities at different locations in the coronary artery, cardiac wall movements, cardiac valve movements, blood flow out off or into the heart chambers, etc.) at a give time are plotted along a bar or line (parallel to the Y axis) such that their position represents to their respective velocities. Ultrasound reflections from different moving objects having similar velocities (Doppler shifts), at any given time, are represented by the same display point.

FIG. 1 is an example of such a Doppler flow velocity display, which is a conventional display of blood flow velocity (Y axis) recorded from the left anterior descending coronary artery as a function of time (X axis). The power of the received ultrasound signal is given by the color of the points according to the color scale (in dB) depicted at the right of the display. Note that since this application is being submitted in black-and white, the color information is reproduced as grayscale.

A disadvantage of this type of display is that it often does not contain enough information to distinguish between signals originating from different sources that have similar velocities. Thus, the flow velocity pattern of the specific desired target region may not be identified and separated from other signals. The ambiguity in the display interpretation is illustrated in the example given in FIGS. 2A and 2B. The tracings displayed in those two figures of flow velocity signals for two different patients, with R-wave information added to the display (e.g., by superimposing an ECG display on the flow display). The signals denoted with numbers 1-5 may be individual entities, however, this can not be verified. Note that in FIGS. 2A and 2B, "R" denotes the position in time of the R wave of the ECG.

In FIGS. 2A and 2B, Signals 1, 2 & 3 (in FIG. 2A), and 4 & 5 (in FIG. 2B) may represent either coronary flow in the LAD (Left Anterior Descending coronary) during the diastole, flow through the mitral valve into the left ventricle, or heart valve movements, all of which are moving in the same direction (relative to the probe) and are located in the ultrasound beam. Separation between such Doppler signals could theoretically be achieved by pulsed Doppler with Gating that provides information regarding the depth of the reflecting object, (i.e., the distance from the ultrasound probe). Unfortunately, such separation is often impossible in practice as the objects may appear in the same gates. Currently this issue can sometimes be resolved by the use of imaging color Doppler. Here the user can try to include in a selected frame the desired target alone. Once this is achieved, he or she switches to Doppler mode and takes the measurement. This procedure, however, is cumbersome and often unsuccessful. Moreover, as the method relies on an initial imaging stage, the measurements are restricted to a relatively small number of windows where the "view" is not masked by bone (e.g., the ribs & sternum) or lung tissue.

SUMMARY OF THE INVENTION

One aspect of the invention relates to a method of processing and displaying received Doppler signals. In this method, a set of N power spectra corresponding to each of N times is obtained based on the received Doppler signals. Then, of set of pixels is displayed with respect to an X axis and a Y axis so that the X coordinate of each pixel in the set corresponds to a time and the Y coordinate of each pixel in the set corresponds to a quantized power level. An attribute of each pixel in the set (e.g., color or intensity) is set to represent the highest velocity for the time-and-quantized-power-level combination that corresponds to the X and Y coordinates of each pixel in the set.

Another aspect of the invention relates to a method of processing received Doppler signals. In this method, a set of N power spectra corresponding to each of N times ($t=t_1 \ldots t_N$) is obtained based on the received Doppler signals. Then, for each of the power spectra in the set, the following steps are performed: (a) determining the power at each velocity V, (b) quantizing the power to K power levels, (c) selecting, from results of the determining and quantizing steps, the highest velocity that corresponds to each of the K power levels, and (d) generating a bar on a display medium, wherein each position along the Y axis of the bar denotes a power level, and an attribute (examples include, but are not limited to, color and intensity) of the bar at any given height is used to denote the velocity selected in the selecting step for a power level corresponding to the given height, and wherein the bar is positioned along the X axis such that the distance along the X axis corresponds to the time t of the corresponding power spectrum.

Another aspect of the invention relates to an apparatus for processing and displaying received Doppler signals that includes a processor and a display. The processor is programmed to obtain, based on the received Doppler signals, a set of N power spectra corresponding to each of N times ($t=t_1$ ... $t_N$). For each of the power spectra, the processor does the following: (a) determines the power at each velocity V, (b) quantizes the power to K power levels, (c) selects the highest velocity that corresponds to each of the K power levels, and (d) generates signals to create a bar on the display, wherein each position along the Y axis of the bar denotes a power level, and an attribute of the bar at any given height is used to denote the selected velocity for a power level corresponding to the given height, and wherein the bar is positioned along the X axis such that the distance along the X axis corresponds to the time t of the corresponding power spectrum.

DESCRIPTION OF THE PREFERRED EMBODIMENTS

The embodiments described herein improve the diagnostic power of the Doppler ultrasound technology in evaluating the anatomical and functional state of the coronary arteries, other parts of the heart, body or in general other systems that incorporate flow. Although the invention is described herein in the context of coronary artery flow, it may also be used in other applications, as will be appreciated by persons skilled in the relevant arts.

Conventional velocity vs. time sonograms are typically obtained by implementing the following preliminary steps: (1) outputting ultrasound pulses; (2) receiving return signals; (3) obtaining the Doppler shifts; and (4) obtaining the power spectra. After these four preliminary steps, the power spectra are processed to generate and display velocity vs. time, with power displayed as color.

In contrast, the new type of display described herein is generated that depicts the ultrasound power (on the Y axis) as a function of time (X axis), and the flow velocity is represented by the color of the displayed points (i.e., with different colors representing different velocities). In alternative embodiments a grey scale may be used instead of color (i.e., with different intensities representing different velocities).

The same spectrograms that are used as the basis of the conventional velocity vs. time displays are used as the basis for the new power vs. time displays. Thus, the same four preliminary steps discussed above are used for the embodiments described herein. These steps may be implemented using conventional approaches that are well known in the field. After these preliminary steps are done, the subsequent processing is different, as described below.

The desired display has power on the Y axis and time on the X axis, and displays velocity in color. This mapping may initially appear to be problematic because there may be situations in which multiple velocities are present at a given power. But this apparent problem is surmounted as follows: The power is quantizing to K levels. Although one suitable step size for performing quantization is 1 dB per step, other step sizes (e.g., ½ dB per step or 2 dB per step) may be used. After the quantization, any time a situation arise in which in which multiple velocities are present at a given power, only the highest velocity is selected for display. This is illustrated schematically in FIG. 3B, where in the power spectrum for Time $t_1$, at a given power P1, there are two velocities V1 and V2 (corresponding to data points B and E, respectively). Since V2 is greater than V1, data point B is ignored, and only the remaining data points A, C, D, E, and F are used to generate the bar 36 on the display, with the color on each point of the bar being set based on the velocity of the data point. Note that while the vertical bars are spaced widely apart in FIG. 3B, they are preferably spaced much closer together in practical systems.

Figure 3A:
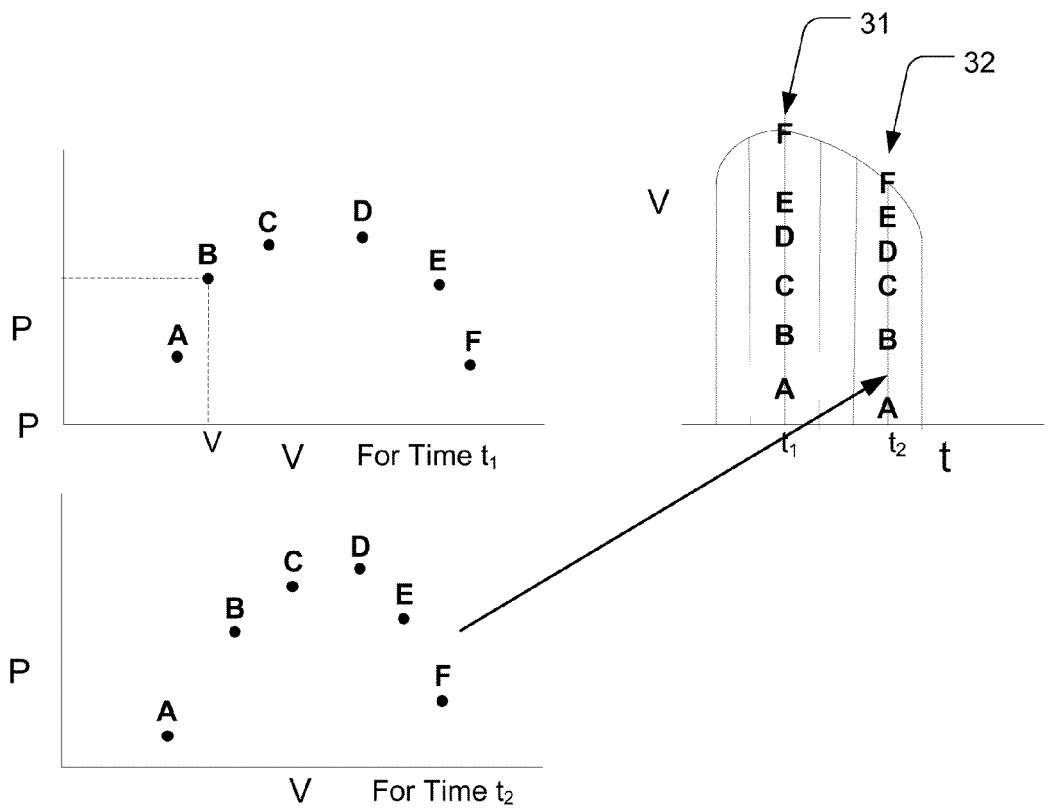
FIG. 3A is a schematic illustration on how lines in conventional Doppler flow velocity displays are generated.
Figure 3B:
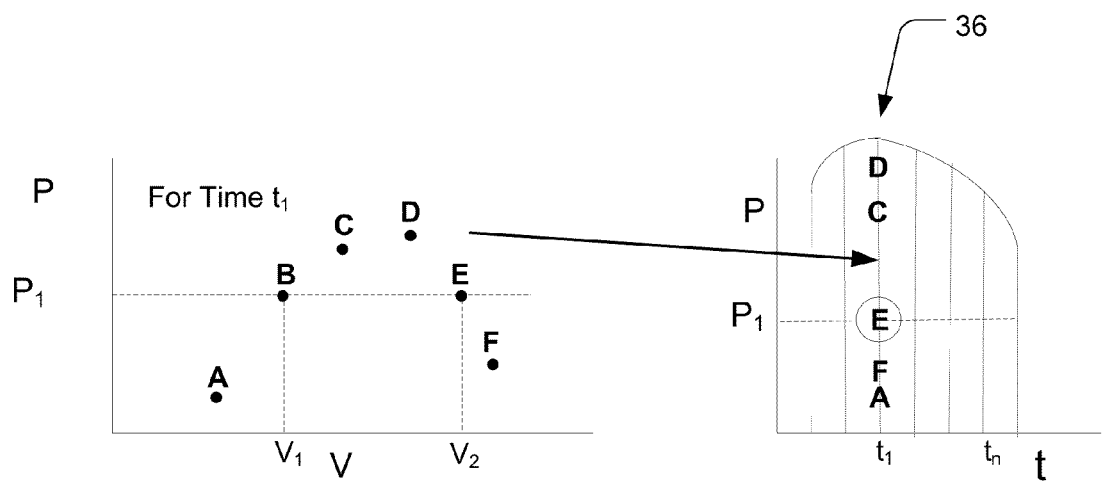
FIG. 3B is a schematic illustration on how lines in the power sonograms are generated.

Note how the schematic illustration for the power vs. time display described above in connection with FIG. 3B differs from the velocity vs. time display that is used for conventional sonograms. For the latter case, All the data points A-F are used to construct each bar 31, 32 as depicted in FIG. 3A because there will always be only one power for any given velocity in any single power spectra.

Figure 4A:
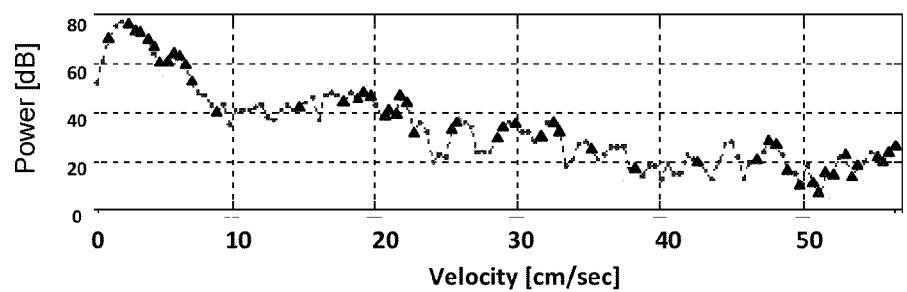
FIG. 4A is a modified power spectrum for a particular time.
Figure 4B:
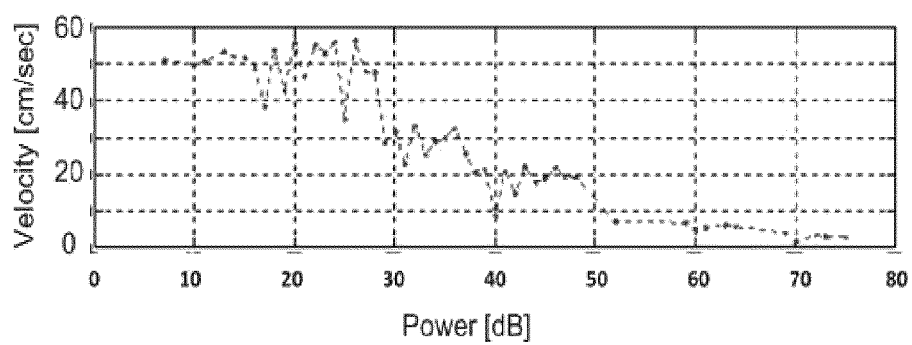
FIG. 4B shows the modified power spectrum of FIG. 4A with certain data points removed and with the axes flipped.

Returning to the power vs. time display, FIGS. 4A and 4B illustrate another example of which data points are ignored when generating the new type of display. FIG. 4A is similar to a conventional power spectrum for a particular time $t_X$, except that in every instance where there are more than one velocity that corresponds to a given power quantization level, the highest of those velocities is indicated by a triangle. Those values are marked with a triangle are selected for subsequent display in the new power vs. time sonogram, and the remaining data points (indicated by circles) are ignored.

After all the data points indicated by circles are ignored, there will never be more than one velocity that corresponds to any given power. Because of that, the axes can be flipped, resulting in the trace shown in FIG. 4B. In FIG. 4B, there is only one velocity that corresponds to each power. Those velocities are then mapped onto a color based on a color key. After this mapping, each quantized power level from 1 to K will have a single color associated with it. A vertical display bar is then constructed with the appropriate color at the height that corresponds to the power levels 1 to K, respectively, for that particular time $t_X$.

Figure 6:
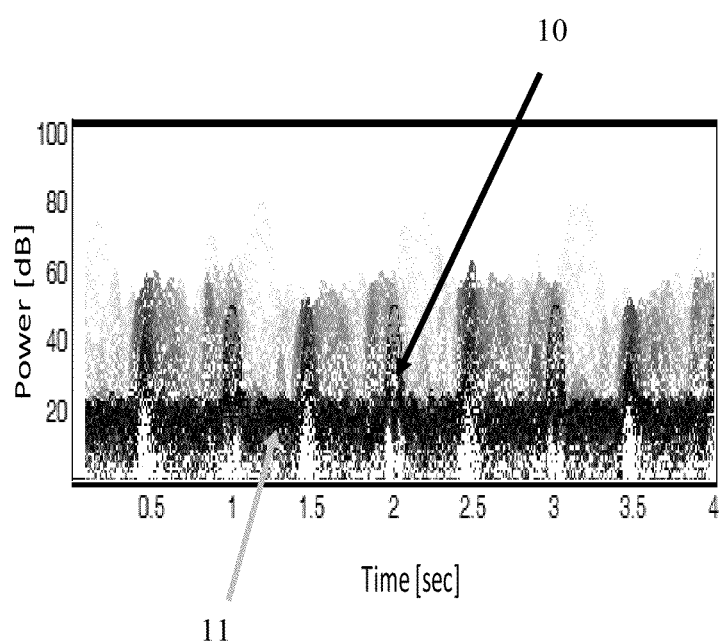
FIG. 6 is an example of a power sonogram display in accordance with some of the embodiments described herein.

The process described above is repeated for the entire interval in question (i.e., for each discrete time between the start time $t_A$ and the end time $t_B$), and each repetition results in the generation of one more vertical bar. These vertical bars are then lined up next to each other in time order to form the final output display, as shown in FIG. 6. In this display, the velocity at each point represented by the color of the point on the display. These graphs are referred to herein as "power sonograms." Preferably, the color code is also displayed (e.g., by displaying a bar alongside the power sonogram that maps the colors onto corresponding velocity values). A variety of different media may be used to present the display to the viewer, including but not limited to computer monitors and paper printouts. A variety of different formats may also be used for the display including color on a black background, color on a white background grayscale on a black background, grayscale on a white background. Alternatively, instead of using color, the density of dots on the display can be used to indicate velocity (e.g., by using lower densities to indicate lower velocities and higher densities to indicate higher velocities). When dot density is used, the use of a black background is preferred.

Figure 5:
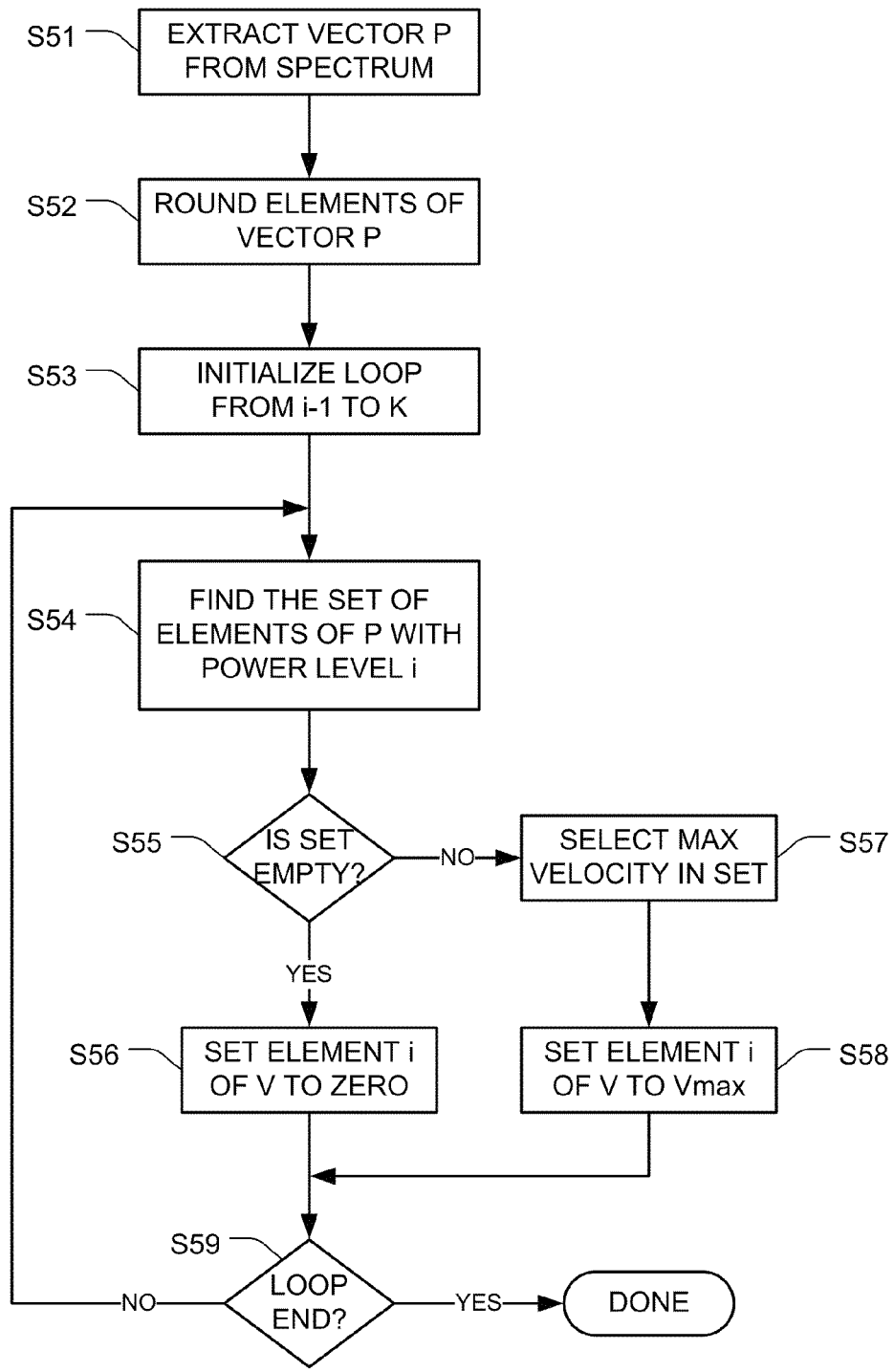
FIG. 5 is a flowchart of an algorithm for generating a single bar on the output display, corresponding to a particular time.

FIG. 5 is a flowchart of a suitable algorithm for generating a single bar on the output display, corresponding to a time $t_i$. In step S51, a vector P of spectral densities for a range of velocities for the time $t_i$ is extracted from the spectrogram that corresponds to that time $t_i$. Next, in step S52, the elements of P are rounded to natural numbers. The steps that follow assume that (1) a range of power levels values is defined: {power$_1$, power$_2$, ..., power$_i$, ..., power$_K$}={1, 2 ..., i, ..., K} where K is the maximal power value in the spectrogram for the time $t_i$; (2) an empty vector V of length K is set up, to be filled with velocity values for a range of powers at the specific time $t_i$; and (3) an empty matrix is set up, to be filled by velocity values for each power and time.

Step S53 is the start of a loop that will process each power level in turn. In step S54, a set $\{p_M\}$ of all the elements of the vector P that correspond to the current power level are identified. If $\{p_M\}$ is empty, processing proceeds to step S56, where the element i of the vector V is set to zero. If $\{p_M\}$ is not empty, processing proceeds to step S57, where the maximum velocity ($V_{MAX}$) in the vector P that matches the current power level is identified, and that maximum velocity is loaded into element i of the vector V in step S58. Processing then proceeds to step S59, where a test is done to see if the last power level has been processed. If more power levels remain, the next power level is processed. But if no more power levels remain, then the output vector V for the time $t_i$ is complete.

Each element of this output vector V is mapped to a color based on the value of $V_{MAX}$ (or the 0) stored in that element. That color information is then used to generate a vertical bar or line of a display, with a height K. Each position along the Y axis corresponds to a particular power from 0 to K, and the color at each point along the bar is set to the color that corresponds to the $V_{MAX}$ for that power. Thus, each position along the Y axis of the bar denotes a power level, and the color of the bar at any given height denotes the selected velocity for the power level corresponding to that height.

Note that since FIG. 5 is a flowchart for generating a single bar on the output display, the algorithm must be run N times to generate the entire display for all times $t_1 \ldots t_N$. The resulting bars are then laid out next to each other, with the bars positioned along the X axis such that the distance along the X axis corresponds to the time t of the power spectrum from which the bar resulted. The result is the entire display shown in FIG. 6.

Figure 1:
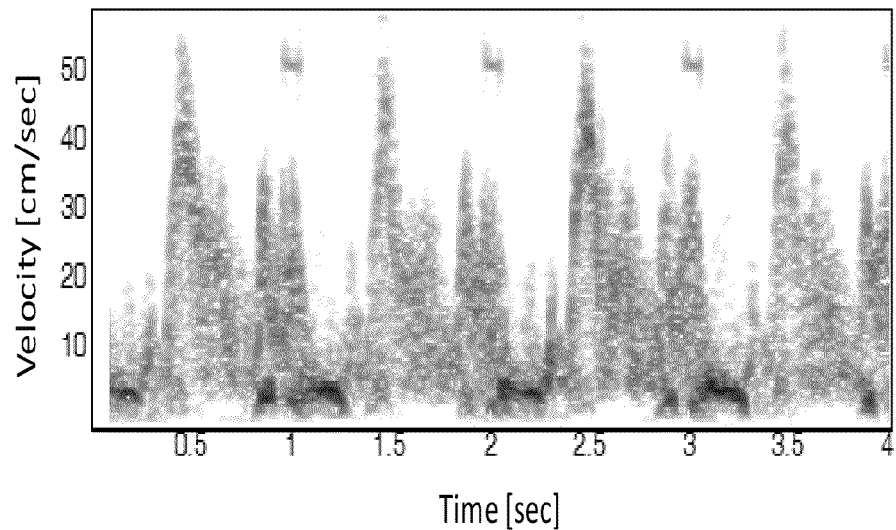
FIG. 1 is an example of a conventional Doppler flow velocity display.

In the example of FIG. 6, the thick wide structure 11 represents the low power high frequency noise. The taller peaks 10 represent the power of the coronary flows depicted by the peaks in FIG. 1.

Figure 2A:
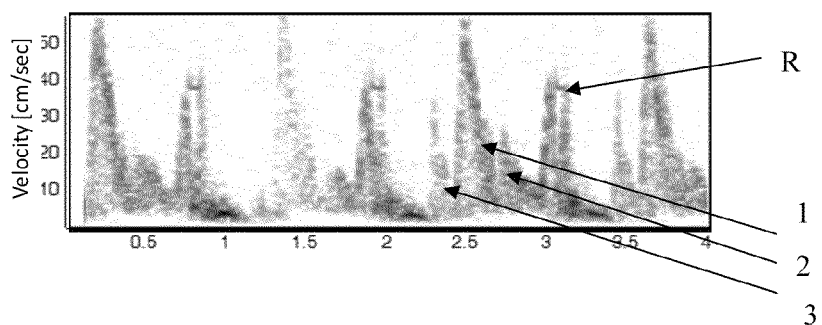
FIGS. 2A and 2B depict conventional Doppler flow velocity displays for two different patients.
Figure 2B:
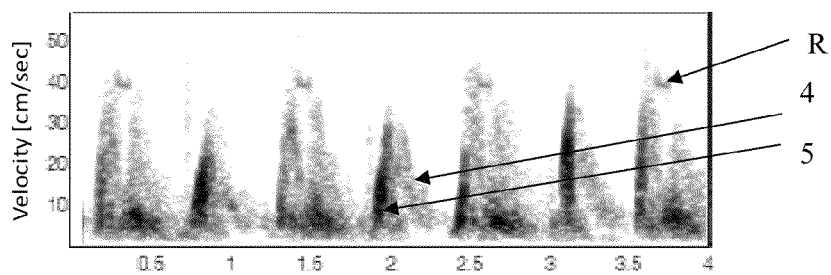

FIGS. 7A, 7B, 8A, and 8B illustrate how the power sonograms can help differentiate between signals of different origin, (e.g., those shown in the standard sonograms in FIGS. 2A and 2B which were not distinguishable using conventional sonograms). In particular, the additional information contained in the new power sonograms 7B and 8B provides additional insight on the relevant anatomical situation.

Figure 7A:
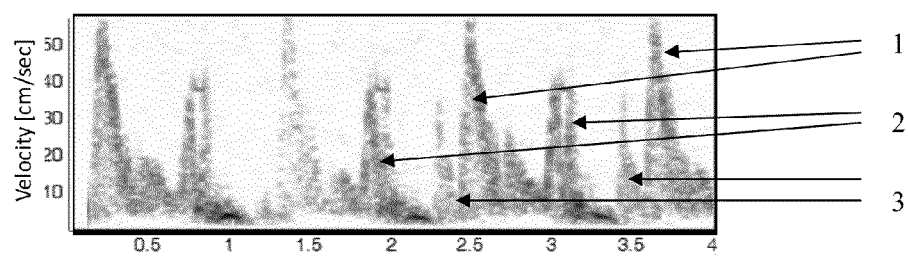
FIGS. 7A and 7B depict a conventional Doppler flow velocity display being displayed on the same screen as a power sonogram display for a first patient.
Figure 7B:
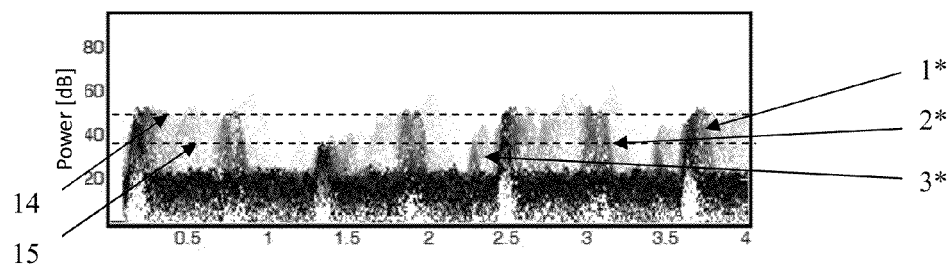

FIGS. 7A and 7B are, respectively, the conventional sonogram and the power sonogram for a coronary artery (LAD) flow velocity tracing in a particular patient over time. Note that FIG. 7A is the same standard sonogram that was depicted in FIG. 2A, with three flow velocity signals marked: 1, 2, & 3. Based on the FIG. 7B power sonogram, we see that the flow signals fall into two groups. One group that includes signals 1 and 2 has corresponding power signals 1* and 2* that have a fixed amplitude corresponding to line 14. The second group signals 3 and corresponding power signals 3* have a distinctly different power given by line 15.

This format for displaying information can be used to help identify the source of the signal (i.e., whether it is flow in a coronary artery, flow in the heart chamber, valve movement, etc.) This is important because the coronary artery flow velocity is often helpful to indicates whether the heart is normal or whether there is stenosis or another problem, etc. A correct estimation can also provide a measure of "coronary flow reserve" that provides very important information about the state of the heart blood perfusion. The coronary flow measurements can also indicate whether there is restenosis after angioplasty, etc. Valve timing also generates artifacts on the power sonograms that enables the user to determine whether the valve is functioning normally.

Figure 8A:
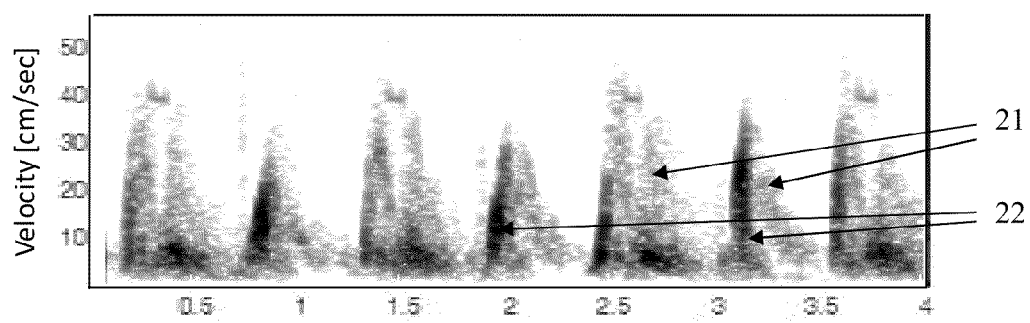
FIGS. 8A and 8B depict a conventional Doppler flow velocity display being displayed on the same screen as a power sonogram display for a second patient.
Figure 8B:
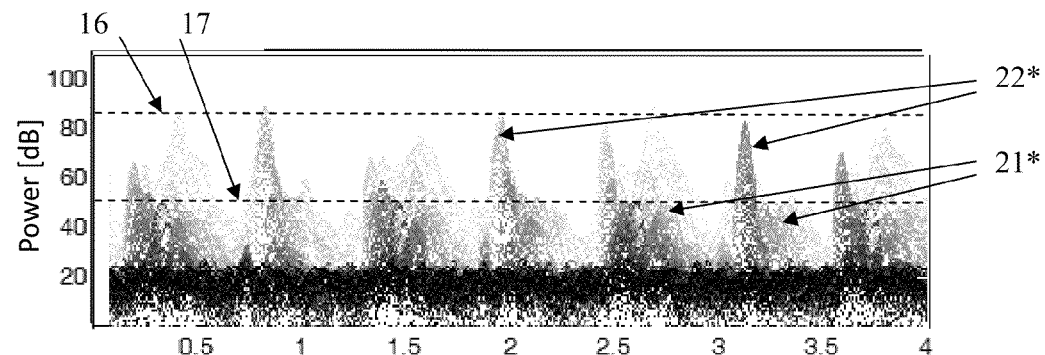

FIGS. 8A and 8B are, respectively, the conventional sonogram and the power sonogram for a coronary artery (LAD) flow velocity tracing of a different patient over time. Note that FIG. 8A is the same standard sonogram that was depicted in FIG. 2B. In FIG. 8A we see two flow velocity signals marked: 21 & 22. In the power sonogram, FIG. 8B, we see that the flow signals fall into two groups. One group that includes signals 21 has Corresponding power signals 21* that have a fixed amplitude corresponding to line 17. The second group signals 22 and corresponding power signals 22* have a distinctly different power given by line 16. The signals marked 21 correspond to coronary artery flow while signals 22 originate from the heart valve movements. The differences between the two power sonograms 7B and 8B therefore provide useful information that can help the viewer distinguish between Doppler signals originating from different sources, which helps the viewer distinguish between various anatomical and functional conditions.

The user of the system can be provided with simultaneous display of the standard Velocity vs. time and the new Power vs. time tracings, or alternatively, only one display (based on the user's choice). When both are provided, processing for each type of output may be implemented either in parallel or serially. Preferably, when both displays are provided simultaneously, they are displayed in windows directly above and below one another, so the two displays are aligned with each other in time (similar to the way FIGS. 7A AND 7B are aligned on the page). In that case, if the user notices something interesting in one of the windows, they can easily find the corresponding part of the other window to obtain additional information about the subject being observed.

Optionally, the start and stop times $t_A$ and $t_B$ for the sonogram may be selected based on an ECG that is taken while the ultrasound returns are being obtained. The ECG is useful for correlating the timing of the Doppler signals and their analysis with the heart beat. It can also be used for synchronization of various activities with the heart cycle. One suitable set of steps for implementing this approach would include: (1) receiving an ECG signal, (2) identifying the R and T waves in the ECG in preparation for analysis; (3) determining the heart cycle duration and the corresponding systolic & diastolic durations as a fraction of the cycle; (4) averaging the above for a number of cycles; (5) selecting the time window to be analyzed (for example 10%-90% of diastole); and (6) defining $t_A$ and $t_B$ as the times at which the analysis begins and ends, respectively. Note that for convenience, this interval $t_A \ldots t_B$ can be renumbered as $t_1 \ldots t_N$, where N=(B−A)+1.

In alternative embodiments, instead setting a pixel on the output display to a particular color to denote a particular velocity, the system may be implemented by using grayscale instead, in which case the display pixels will be set to a particular intensity to denote a particular velocity, as will be appreciated by persons skilled in the relevant arts. Note that since the figures in this application are monochrome, they can be viewed as examples of this grayscale embodiment.

Optionally, the power sonogram and the conventional spectrogram can be further processed by (1) defining and displaying power levels originating from different sources, and (2) defining and displaying the duration of different velocity and power phenomena. Correlations can then be searched for between the phenomena defined by their power characteristics and those defined by their velocity characteristics. This may be accomplished by parameterizing the data and then performing classification using a suitable conventional classification algorithm, making reference to known anatomic conditions of the test subjects. This additional processing can provide the user with parametric information regarding the characteristics of the selected flows which were identified and separated using the characteristic differences in the velocity, timing, duration as well as other temporal characteristics and the corresponding power characteristics and the relationships between all of the above. The output of these analyses can be graphical and/or numeric.

The above-describe methods are preferably implemented using conventional processing and display hardware, but with the processing section programmed to implement the above-describe algorithms instead of the conventional sonogram algorithms.

Numerous modifications to the above-described embodiments will be apparent to those skilled in the art, and are also included within the purview of the invention.

I claim:

1. A method of processing and displaying received Doppler signals, the method comprising the steps of:
    obtaining, based on the received Doppler signals, a set of N power spectra corresponding to each of N times; and
    displaying of set of pixels with respect to an X axis and a Y axis so that the X coordinate of each pixel in the set corresponds to a time and the Y coordinate of each pixel in the set corresponds to a quantized power level, wherein an attribute of each pixel in the set is set to represent the highest velocity for the time-and-quantized-power-level combination that corresponds to the X and Y coordinates of each pixel in the set, and
    wherein, when the attribute of each pixel in the set is set, velocities that are lower than the highest velocity for the time-and-quantized-power-level combination that corresponds to the X and Y coordinates of each pixel are disregarded.

2. The method of claim 1, wherein the attribute is color, and the color of each pixel in the set is set to represent the highest velocity for the time-and-quantized-power-level combination that corresponds to the X and Y coordinates of each pixel in the set.

3. The method of claim 1, wherein the attribute is intensity, and the intensity of each pixel in the set is set to represent the highest velocity for the time-and-quantized-power-level combination that corresponds to the X and Y coordinates of each pixel in the set.

4. The method of claim 1, further comprising the step of displaying a standard sonogram in which position along the Y axis is used to denote velocity, and color is used to denote power.

5. The method of claim 4, wherein the standard sonogram in aligned with respect to the displayed set of pixels so that the time scale of the standard sonogram lines up vertically with the time scale of the displayed set of pixels.

6. An apparatus for processing and displaying received Doppler signals comprising:
    a processor; and
    a display,
    wherein the processor is programmed to obtain, based on the received Doppler signals, a set of N power spectra corresponding to each of N times ($t=t_1 \ldots t_N$), and for each of the power spectra,
        (a) determine the power at each velocity V,
        (b) quantize the power to K power levels,
        (c) select the highest velocity that corresponds to each of the K power levels and disregard the velocities that are lower than the highest velocity for each of the K power levels, and
        (d) generate signals to create a bar on the display, wherein each position along the Y axis of the bar denotes a power level, and an attribute of the bar at any given height is used to denote the selected velocity for a power level corresponding to the given height, and wherein the bar is positioned along the X axis such that the distance along the X axis corresponds to the time t of the corresponding power spectrum.

7. The apparatus of claim 6, wherein the attribute is color, and the color of the bar at any given point is set to represent the highest velocity for the time-and-quantized-power-level combination that corresponds to the X and Y coordinates of the given point.

8. The apparatus of claim 6, wherein the attribute is intensity, and the intensity of the bar at any given point is set to represent the highest velocity for the time-and-quantized-power-level combination that corresponds to the X and Y coordinates of the given point.

9. The apparatus of claim 6, wherein the attribute is dot density, and the density of dots on the bar at any given point is set to represent the highest velocity for the time-and-quantized-power-level combination that corresponds to the X and Y coordinates of the given point.

10. The apparatus of claim 6, wherein an increase in position along the X axis corresponds to an increase in time, according to a linear relationship, and wherein an increase in position along the Y axis corresponds to an increase in power.

11. The apparatus of claim 6, wherein the power is quantized to K levels by rounding off to natural numbers, measured in dB.

12. The apparatus of claim 6, wherein the processor is further programmed to generate signals that produce a standard sonogram on the display, in which position along the Y axis is used to denote velocity, and the attribute is used to denote power.

13. The apparatus of claim 12, wherein the standard sonogram is aligned on the display with respect to the generated bars so that the time scale of the standard sonogram lines up vertically with the time scale ($t_1 \ldots t_N$) of the generated bars.

* * * * *